(12) United States Patent
Jiang et al.

(10) Patent No.: US 9,031,203 B2
(45) Date of Patent: May 12, 2015

(54) X-RAY BEAM SYSTEM OFFERING 1D AND 2D BEAMS

(71) Applicant: Rigaku Innovative Technologies, Inc., Auburn Hills, MI (US)

(72) Inventors: Licai Jiang, Rochester Hills, MI (US); Boris Verman, Bloomfield, MI (US)

(73) Assignee: Rigaku Innovative Technologies, Inc., Auburn Hills, MI (US)

( * ) Notice: Subject to any disclaimer, the term of this patent is extended or adjusted under 35 U.S.C. 154(b) by 179 days.

(21) Appl. No.: 13/912,364

(22) Filed: Jun. 7, 2013

(65) Prior Publication Data
US 2013/0329861 A1 Dec. 12, 2013

Related U.S. Application Data

(60) Provisional application No. 61/657,446, filed on Jun. 8, 2012.

(51) Int. Cl.
*G21K 1/06* (2006.01)
*G01N 23/201* (2006.01)
(52) U.S. Cl.
CPC .............. *G21K 1/067* (2013.01); *G01N 23/201* (2013.01); *G21K 2201/064* (2013.01)
(58) Field of Classification Search
CPC G21K 1/067; G21K 2201/064; G01N 23/201
USPC ........................ 378/148, 147, 83–90, 73, 78
See application file for complete search history.

(56) References Cited

U.S. PATENT DOCUMENTS

| 5,016,267 | A  | * | 5/1991  | Wilkins ........................... 378/84 |
| 6,014,423 | A  |   | 1/2000  | Gutman et al. |
| 6,041,099 | A  |   | 3/2000  | Gutman et al. |
| 6,807,251 | B2 |   | 10/2004 | Okanda et al. |
| 7,646,849 | B2 | * | 1/2010  | Iwasaki et al. .................. 378/86 |
| 8,094,780 | B2 |   | 1/2012  | Jiang |
| 2011/0085644 | A1 | * | 4/2011 | Verman et al. ................ 378/147 |
| 2011/0268251 | A1 |   | 11/2011 | He |
| 2012/0140897 | A1 |   | 6/2012 | Bruegemann et al. |

OTHER PUBLICATIONS

Notification of Transmittal of the International Search Report and the Written Opinion of the International Search Authority, or the Declaration, International Application No. PCT/US2013/044659, Dated Aug. 14, 2013.
53$^{rd}$ Annual Denver X-ray Conference, SAXSess—An Analytical Tool for Nanostructured Materials, Aug. 2-6, 2004, Sheraton Steamboat Resort, Steamboat Springs, Colorado.
Anton Paar Brochure, SAXSpace—The modular solution for nanostructure analysis, Nov. 2012, 14 pgs.
Anton Paar Brochure, SAXSess mc$^2$ —The Modular Tool for Nanostructure Analysis, 2003, 16 pgs.

* cited by examiner

*Primary Examiner* — Irakli Kiknadze
(74) *Attorney, Agent, or Firm* — Brinks Gilson & Lione

(57) ABSTRACT

A system for analyzing a sample is provided. The system includes an optical system capable of providing a one-dimensional beam and a two-dimensional beam. The system may include a beam selection device to select between providing a one-dimensional x-ray beam to the sample in a one-dimensional operation mode and a two-dimensional x-ray beam to the sample in a two-dimensional operation mode.

19 Claims, 7 Drawing Sheets

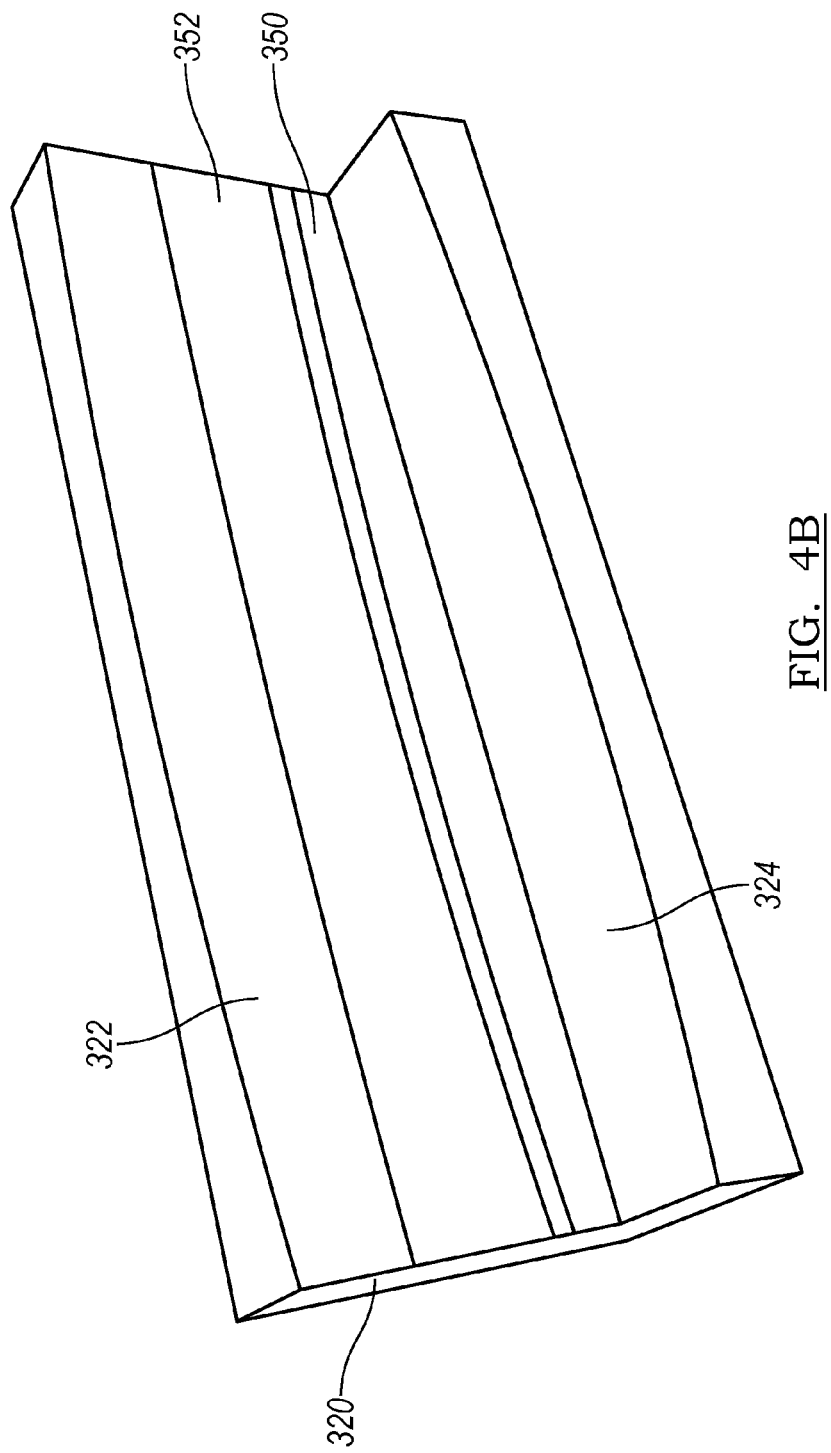

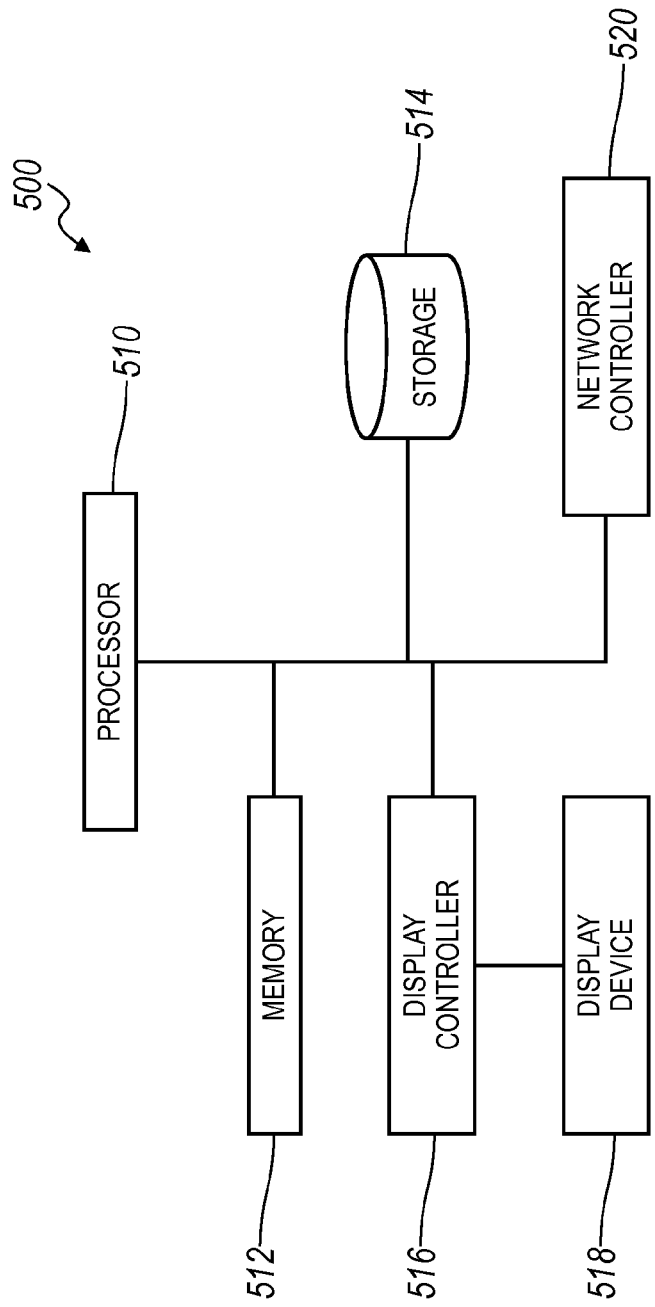

X-RAY BEAM SYSTEM OFFERING 1D AND 2D BEAMS

CROSS REFERENCE TO RELATED APPLICATIONS

This application claims the benefit of U.S. Provisional Patent Application No. 61/657,446 filed Jun. 8, 2012, the content of which is hereby incorporated by reference in its entirety.

BACKGROUND

Field of the Invention

The present application generally relates to an optical system with one-dimensional capability and two-dimensional capability for x-ray diffraction or x-ray scattering systems.

BRIEF SUMMARY

A system for analyzing a sample through x-ray coherent scattering and diffraction is provided. The system includes a beam subsystem offering the capability of providing both a one-dimensional beam, a two-dimensional beam, and possibly a divergent beam, and a selection device for selecting the one-dimensional beam for a one-dimensional operation mode or the two-dimensional beam for a two-dimensional operation mode or a divergent beam for Bragg Brentano configuration.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIGS. 4A and 4B are a schematic illustration of an optical system for an x-ray scattering or diffraction system using a point source;

FIG. 5 is a schematic view of a processing system for implementing the methods described herein.

DETAILED DESCRIPTION

Figure 1:
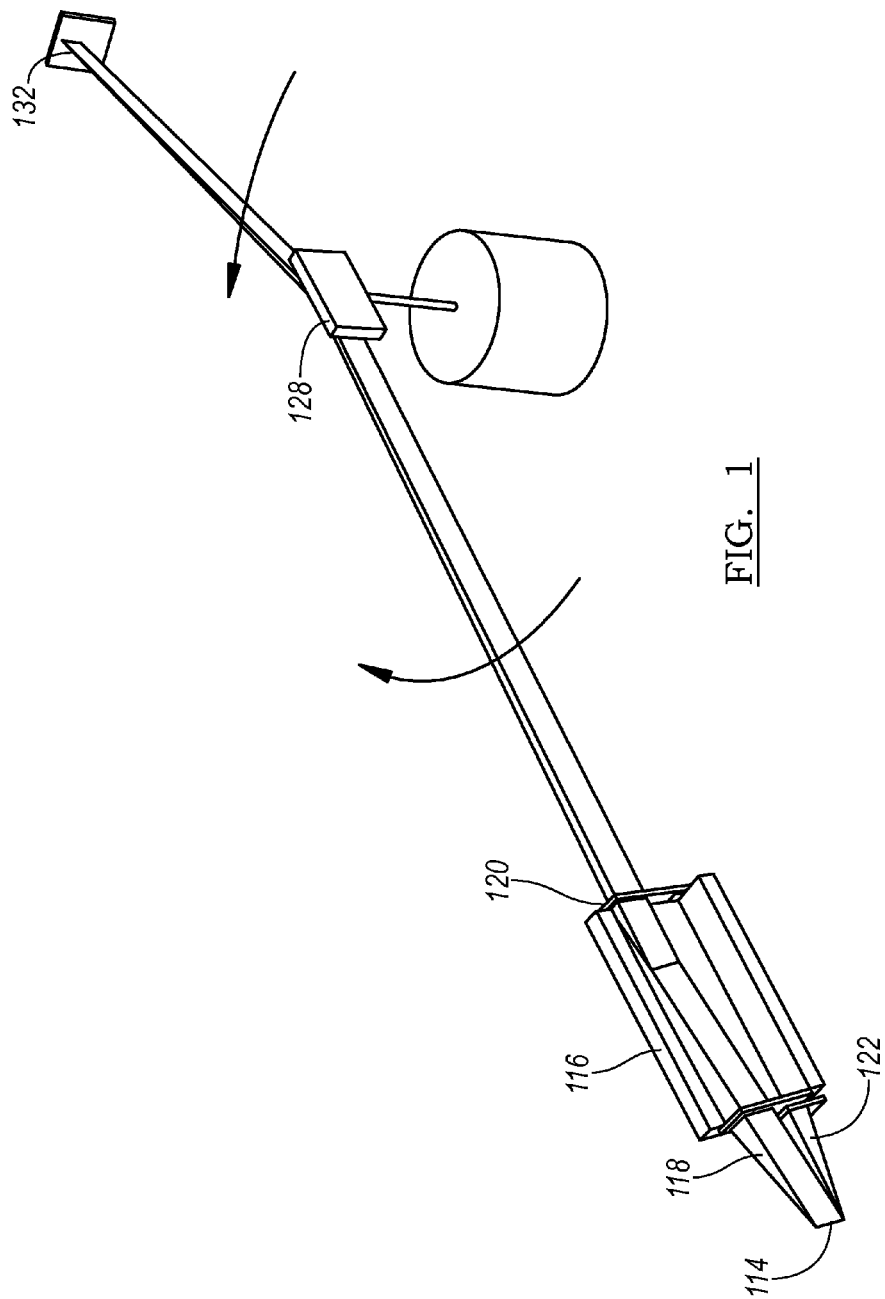
FIG. 1 is a schematic illustration of an x-ray scattering or diffraction system in the one-dimensional mode.

For an x-ray scattering or diffraction system, the essential performance is typically characterized by the speed (proportional to flux), the signal-to-noise (spectral purity or background related characteristics), and the resolution (often can be characterized as the beam diameter at the detector position divided by the sample-to-detector distance, or divergence of the beam). In general, there are two distinctive types of x-ray coherent scattering based systems. One is typically called powder diffraction system and the other one is called single crystal diffractometer. A typical powder diffractometer uses a line source for its great intensity on sample. A typical single crystal diffractometer uses a point source for the needed spatial definition, e.g. low divergence in both directions perpendicular to the beam's propagation. Modern diffractometers use various optical elements to improve the performance. These improvements include increasing flux by collimating or focusing the beam, reducing background through the improved spectrum purity, and improving resolution by focusing the probe beam towards detector position or reducing the divergence of a parallel beam. A typical powder diffractometer uses a one-dimensional optic to condition the beam. Such an optic usually takes the form of a parabolic cylinder mirror to collimate the beam or the form of an elliptical cylinder mirror to focus the beam. These mirrors follow either an elliptical contour or a parabolic contour in the plane of reflection/diffraction and straight line in the direction perpendicular to the reflection/diffraction direction. A single crystal diffractometer usually uses a two-dimensional optic for conditioning the beam. Both ellipsoidal optic and paraboloidal optic are examples of two-dimensional optics. An ellipsoidal optic forms a focused beam from a divergent beam; and a paraboloidal optic forms a collimated beam from a divergent beam. Another type of widely applicable two-dimensional optics involves two mirrors, each mirror reflects, either focuses or collimates, x-rays in one of the two orthogonal directions perpendicular to the x-rays propagation. Together the optic system alters the divergence in the two orthogonal directions and thus achieves the objective of conditioning the beam in two dimensions. The well-known Kirkpatrick Baez (KB) and its variation "side-by-side" KB systems follow this principle. Typical mirrors in such a system include elliptical cylinder mirror and parabolic cylinder mirror. Multilayer optics, owing to its ability of capturing high flux and naturally monochromatizing the beam with very low spectral background, has been widely adopted in the instruments of x-ray scattering and diffraction.

Natural forms of majority substances are in the powder forms of crystallized structures. Powder diffractometer is a powerful analytical instrument for quickly analyzing powder characteristics such as structure, phase, texture, stress and so on. Single crystal diffractometer on the other hand is the instrument investigating complicated structure such as the structures of highly complex protein molecules. As the designs and the characteristics of the two types of diffraction systems are largely different, it requires one to own both systems in order to acquire both the one-dimensional and the two-dimensional capabilities. A single instrument having both the one-dimensional and the two-dimensional capabilities would improve the throughput for some applications and drastically reduce the cost as well.

To address these issues, one may first address the issue associated with the probe beam. The characteristics of the probe beam determine the nature of the diffraction system. Further, a two-dimensional detector, although not a necessary element for the fundamental function, is a widely adopted detection element for improving the speed of the instrument.

A dual mode x-ray scattering or diffraction system may be created that includes a source, an optic, a beam selection device and a detector. The source may emit an x-ray beam that is reflected by the optic to form two beams or three beams towards a sample. One of the beams can be a two-dimensional beam for which the divergence is controlled in two orthogonal directions perpendicular to the beam propagation direction. Another beam may be a one-dimensional beam for which the divergence is controlled in one direction only, and the beam is not controlled and/or still divergent in the other direction. The third beam may be a divergent beam for Bragg Brentano configuration. A beam selection mechanism may be inserted either between the source and the optic, or between the optic and the sample for selecting a beam. A detector may detect the scattered or diffracted x-rays from the sample. The selected beam determines the mode of the system, either providing a one-dimensional mode or a two-dimensional mode of the operation. The system may also be equipped with a sample goniometer to provide sample spin or rotation for single crystal applications which are normally carried out by two-dimensional diffractometers. As a typical powder diffractometer, the system could be equipped with a goniometer, with the detector mounted on one arm which is rotatable about the goniometer's center, and the source and the optic mounted on another arm which is also rotatable about the goniometer. These motion freedoms enable the θ-θ and θ-2θ scans with the 1-dimensional mode.

Typical two-dimensional beams include two-dimensional focused beam which forms a tight spot at its focus, and two-dimensional collimated beam with low divergence in the directions perpendicular to the propagating beam. The divergence is typically determined by the source size and the rocking curve width of the optic if the optic is a diffractive optic such as crystal optic or multilayer optic.

Typical one-dimensional beams include a fan beam of which the source is a point source and the divergence is controlled in one direction only, and a "line" beam of which the source is a line source and the divergence is controlled in one direction only. A one-dimensional beam typically has a "line" profile at the sample position and the detector position, with dimension in one direction much longer than in the other direction. The ratio is at least 1:4, and typically 1:8 or more. For a one-dimensional beam, the beam can be either focused or collimated in the direction that the divergence is controlled.

U.S. Pat. No. 6,041,099 describes a side-by-side Kirkpatrick Baez (KB) optic for forming a two-dimensional beam. The beam is reflected by both reflectors in two orthogonal directions substantially perpendicular to the beam propagation direction. The working zone for the two-dimensional optic is a narrow strip on each mirror along the junction line of the two reflectors, typically about a few millimeters wide at most depending on the x-ray energy, d-spacing range, and the mirror length.

However, a dual mode optical system can be designed by using two one-dimensional mirrors. One of the mirrors should be sufficiently wide for providing both the one-dimensional reflection, and coupled with the other mirror in Kirkpatrick-Baez configuration, preferably the side-by-side configuration, to provide a two-dimensional beam. It may be preferred to have an aperture with two openings attached on the entrance side of the optical assembly, or the exit side of the assembly, or both, and a selection device, which can be a blade or a slit, is further incorporated into the optical system for selecting the beam. If a divergent beam is desired for Bragg Brentano configuration, there will be a third opening on the aperture. Aperture(s) attached at the entrance and exit will make the alignment much easier. A four-blade slit can be used to serve as the beam defining aperture as well as the beam selection device. When a point source is used for the dual mode optic design, e.g. one of the mirrors is designed with the width capable of reflecting a one-dimensional beam and a set of apertures (either one aperture at one side or two apertures on the both ends) may be used to form the one-dimensional beam and the two-dimensional beam, where the one-dimensional beam is a fan beam. A fan beam is commonly used for x-ray imaging such as x-ray CT, and has not been used for XRD. Careful analysis shows that a fan beam can also be used for x-ray scattering and x-ray diffraction. Compared to the traditional one-dimensional beam or the line beam, there is not more information loss. The fan beam has a flux higher than the two-dimensional beam. Therefore, if the one-dimensional scattering/diffraction system is suitable for an application or a sample, the one-dimensional mode of the operation has the merit of higher flux thus higher speed. On the other hand, the flux on the sample for a fan beam is likely still much lower than that of a traditional one-dimensional beam since for the latter, the source is long and can have a much higher power loading. One example is that a microfocusing source of 30 um diameter with a copper target may have a power loading 30 W, while a standard Long Fine Focus (LFF) line source has a source projection 40 um×12 mm and has a power loading 2 kW.

When the dual mode optic is used with a line source, the direction of the source along the length of the source can be aligned with the reflector designed for the single reflection. Although the other reflector can be aligned with any point of the source for delivering the two-dimensional x-ray beam, the reflector may be aligned to a point near to the end of the line source when used in the dual mode operation.

It may be preferred to use diffraction optics such as multilayer optics or other bandpass optics such as crystal optics. When the dual mode optic is coupled with a line source, the reflector perpendicular to the line source, e.g. the reflector contributing to the two-dimensional beam only, will reflect x-rays from different parts of the x-ray source at different wavelengths and form a broad and energy dispersive beam. However, the other reflector, as long as it is aligned along the source direction, will form the Bragg condition for the wavelength that it is designed for, and therefore form a clean spectrum and a spatially well-defined two-dimensional beam.

When the dual mode optic is coupled to a point source, the beam selection mechanism, which can be as simple as a plate to let one beam through and block other beams, can be positioned between the source and the optic, or between the optic and the sample. When the dual mode optic is coupled to a line source, the beam selection mechanism is preferably positioned between the source and the optic since otherwise, the x-rays coming from the long source and singly reflected could pass through the aperture of two-dimensional beam and contaminate the 2-dimensional beam.

By arranging the angle between the mirror, which contributes to only the two dimensional beam, and the mirror which contributes to both the two-dimensional beam and the one dimensional beam, one can design a dual mode optical system with specific beam positions. For instance, the center of the two-dimensional beam can be at the center of the one-dimensional beam, either at the sample position or at the detector position. The benefit for both beams centered at the same point at the sample position is that the sample position does not need to be changed when switching between the two operation modes. The benefit for both beams centered at the same spot at the detector position is that data will have the same coordinates.

Sample handling is a notable part of an x-ray scattering or diffraction system if the two beams are not centered on the same point at the sample position. The sample handling system should be able to position the sample both in the paths of the one-dimensional beam and the two-dimensional beam. This may be as simple as mechanical markers for different operation modes and a translation device which can position the sample to different positions pertinent to the operation modes. In the two-dimensional mode, a sample goniometer, which provides the spinning and rotation, may also be implemented. Other sample handling systems, such as grazing incident stages, or sheer-stress cell and many other standard accessories for x-ray diffraction or scattering, can be integrated to the system.

It is preferred to use a two-dimensional detector, such as an x-ray CCD camera, an Image Plate (IP), and a solid state photon counting pixelated detector. A solid state photon counting detector has the merits of high resolution, ultra-low noise, real time and fast counting rate. Even with the one-dimensional operation mode, the two dimensional detector offers the merit of easy alignment. The alignment between line beam and the detector is not as critical for a two-dimensional detector as for a one-dimensional detector, due to the fact that data is collected in two dimensions, and one can find the beam direction from the two-dimensional image.

A one-dimensional detector, which is also called linear detector, can also be used for the scattering or diffraction system as well. Two problems arise with using a one-dimensional detector. For the one-dimensional mode, the line beam is aligned with the detector cell. Otherwise the resolution suffers. For the two-dimensional mode, using a one-dimensional detector is inadequate for acquiring the two-dimensional data directly. One solution would be using a slit in front of the detector and then to scan the data field to create a two-dimensional image. The scanning can be done linearly or angularly with the rotation center at the center of the primary beam. When scanning angularly, the slit opening in front of the detector can be in the form of constant angle, e.g. polar scan. The speed of the diffraction system suffers when using a one-dimensional detector. One of the only merits to use a linear detector might be its low cost, provided that the motion control needed for the scanning is less expensive than the cost difference between a 2D detector and a 1D detector.

The dual mode x-ray scattering or diffraction system allows the system to utilize the full capacity of offering high flux in the one-dimensional mode and two-dimensional capability in the two-dimensional mode at a cost not much higher than one system. Additionally, the dual mode system has a flux density, e.g. the flux per unit area, of the two-dimensional beam higher than that of the one-dimensional beam. Thus for a small sample, using the two-dimensional mode could yield higher signal-to-noise ratio. Some embodiments of the system may also have one or more of the following benefits. When a point source is used, the system may have an optimized two-dimensional performance and yet may offer much higher flux in the one-dimensional mode than in the two-dimensional mode. When a line source is used, the system offers the optimized performance of the one-dimensional mode, and yet offers the two-dimensional capability. One of the examples of the dual mode scattering/diffraction system is Small Angle X-ray Scattering (SAXS) camera. A dual mode SAXS camera will have the merit of the high flux of the one-dimensional Kratky system, and the capability of the two-dimensional pinhole camera when coupled with a Kratky collimation system (U.S. Pat. No. 8,094,780). For many unknown samples, one can quickly try with one of the two operation modes for a quick check and determine which mode is the best for the measurement. The SAXS camera can be used to investigate anisotropic material and can be configured into a high resolution reflectometer, or a high resolution reflective SAXS camera. Since the overall camera length is much shorter than a pinhole camera, the system has a large angular range. The system can be extended from small angle scattering measurement to wide angle scattering measurement.

For powder diffractometers, there are three configurations which use different types of one-dimensional beams. The first type is a focusing beam and is commonly used for powder inserted in a glass or plastic capillary. The second type is a parallel beam. Parallel beam offers precision measurements for samples of more transparent, irregular shaped, and in thin film form, etc. The parallel beam also offers a beam suitable for high resolution diffractometry when further coupled with single crystal channel-cut monochromator. The third type of the incident beam is a divergent beam. The configuration using a divergent beam is called Bragg-Brentano diffractometer and is widely used in powder diffractometry. In Bragg Brentano configuration, the sample directs and focuses the diffracted beams on the focusing circle. The configuration offers high resolution and high sensitivity, but is prone to the errors introduced by irregular surface shape, penetration of x-rays to the sample, and the inaccurate position of the samples. A separate opening parallel to the opening of the one-dimensional beam can be introduced for allowing the direct beam incident upon the sample. Having an opening for a direct beam allows the optical system to utilize three beams: a two-dimensional beam, a one-dimensional collimated or focused beam, and a one-dimensional divergent beam. Typically, the opening for the direct beam, or divergent beam, is a rectangular shaped opening, and positioned in parallel with the opening for the one-dimensional beam and parallel to the direction of the line source. In another word, the position of the opening for the direct beam can be obtained by shifting the position of the opening for the one-dimensional beam in the direction perpendicular to the centering line passing through the opening for the one-dimensional beam and the opening for the two-dimensional beam. A beam selection mechanism allows selection of one beam among the three. In order to improve the spectral quality of the divergent beam, a spectral filter can be used for the divergent beam. Using a divergent beam with a mirror conditioned beam in one optical assembly is disclosed by U.S. Pat. No. 6,807,251.

As such, one embodiment of the envisioned probe beam system includes a source, two one-dimensional reflectors, and an aperture. The two one-dimensional reflectors include a first reflector designed to form a one-dimensional beam. The first reflector is coupled with a second reflector, for example in Kirkpatrick Baez configuration and preferably in a side-by-side configuration, to form a two-dimensional beam. The aperture may have two openings, one for the two-dimensional beam which is reflected by both mirrors and one for the one-dimensional beam which is reflected by one mirror only. In addition, a selection mechanism, either a blade, or a slit, is used for selecting one of the two beams. If a divergent beam is needed, the aperture will have three openings corresponding to the one-dimensionally reflected beam, the two-dimensionally reflected beam and the divergent beam. The beam selection device will select one of the three beams.

A sample carrier may be included to carry the sample to the position of the one-dimensional beam or the position of the two-dimensional beam depending on the operation mode of the system. However, the optical system can be designed such that the one-dimensional beam center coincides with the two-dimensional beam center. In this case, the sample translation for the purpose of switching the operation mode is no longer needed. A sample goniometer for the two-dimensional mode may also be necessary for a diffractometer. The sample goniometer provides the spin or rotation in order to satisfy the Bragg condition for the crystal lattice to diffract x-rays.

Now referring to FIG. 1, one example of a dual mode x-ray scattering or diffraction system is provided. The system is in the one-dimensional mode. The x-ray scattering or diffraction system includes an x-ray source 114, an optic 116, a sample 128, and a detector 132. The x-ray source 114 may be a line source or a point source. The source 114 may emit a divergent beam that is received by an optic 116. Part of the optic 116 may be a two-dimensional optic which conditions the beam in two perpendicular dimensions orthogonal to the beam propagation. Part of the optic may be a one-dimensional optic that conditions the beam in one dimension perpendicular to the direction of propagation. The optic 116 may be a crystal optic or a multi-layer optic. Further, the optic 116 may be a KB side-by-side or sequential optic in part and combined with a one-dimensional optic. A beam selection device 122 may be between the source and the optic when the source is a line source as shown in FIG. 1. For a point source, the beam section device 122 can be either between the source and the optic or between the optic and the sample 128. The beam selection device 122 may be controlled to select various portions of the beam, or where the beam is split, the beam selection device 122 may select one of the split beams. The beam selection device 122 may be a shutter or movable beam stop that is controlled by an actuator to select between a one-dimensional and two-dimensional operation mode. A translation device carries the sample 128 to the one-dimensional beam position or the two-dimensional beam position depending on the system operation mode and also the beam design. The diffracted x-rays may be collected by detector 132. The detector 132 can be mounted on an arm which is able to revolve about an axis. The source and the optic can also be mounted on an arm which is able to revolve about the same axis. These revolving freedoms enable different diffraction configurations: θ-θ scan and θ-2θ scan.

Figure 2:
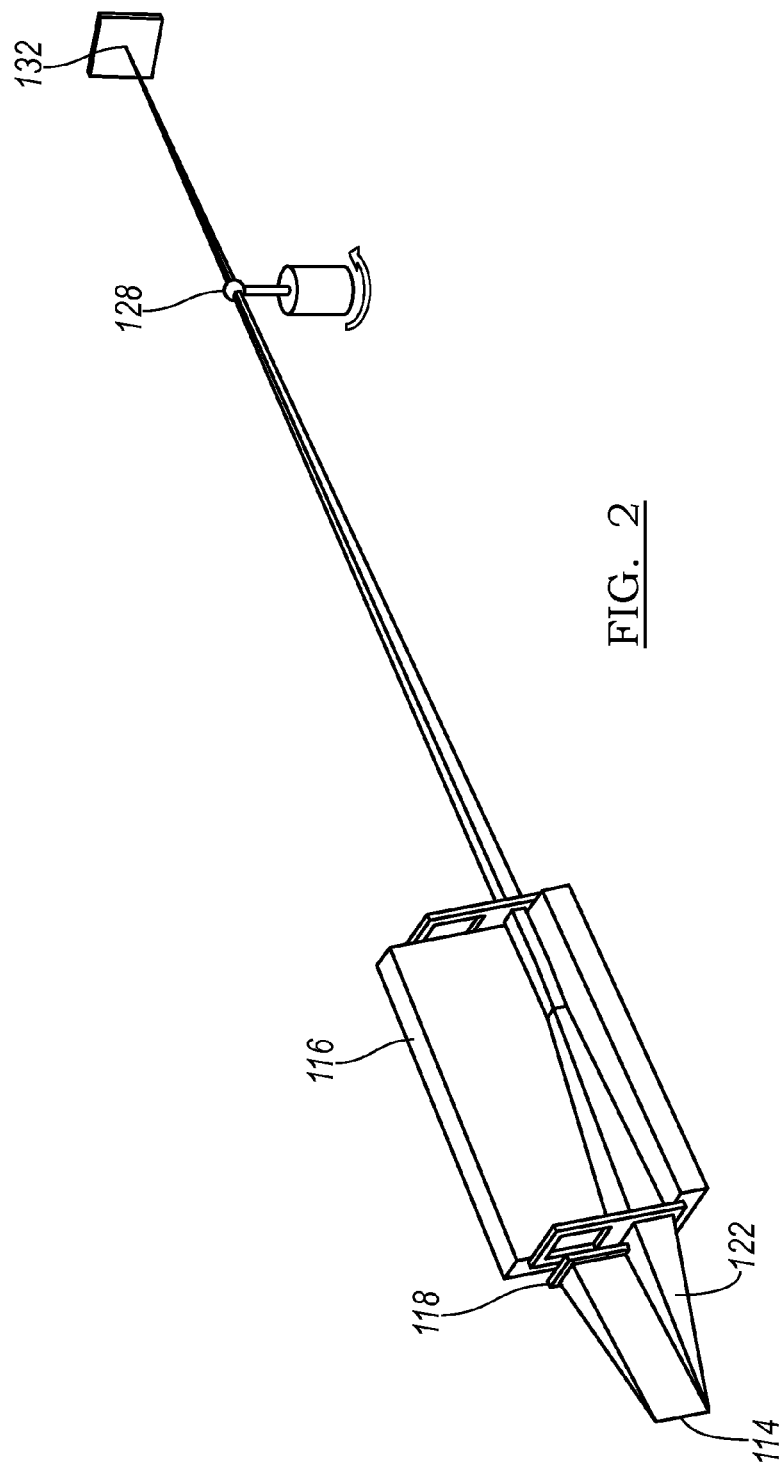
FIG. 2 is a schematic illustration of a x-ray scattering or diffraction system in the two-dimensional mode.

Referring to FIG. 2, the dual mode scattering or diffraction system is in the two-dimensional operation mode. The beam selection device 122 is positioned to block x-rays that form the one-dimensional beam and allows the x-rays that form the two-dimensional beam through. A sample goniometer may spin or rotate the sample 128 when the diffractometer operates in the two-dimensional mode. In addition, the sample 128 may be translated into the two-dimensional beam, if the two-dimensional beam is offset from the one-dimensional beam. In some implementations the beams may be conditioned such that the one-dimensional beam and the two-dimensional beam overlap at the sample position.

Figure 3A:
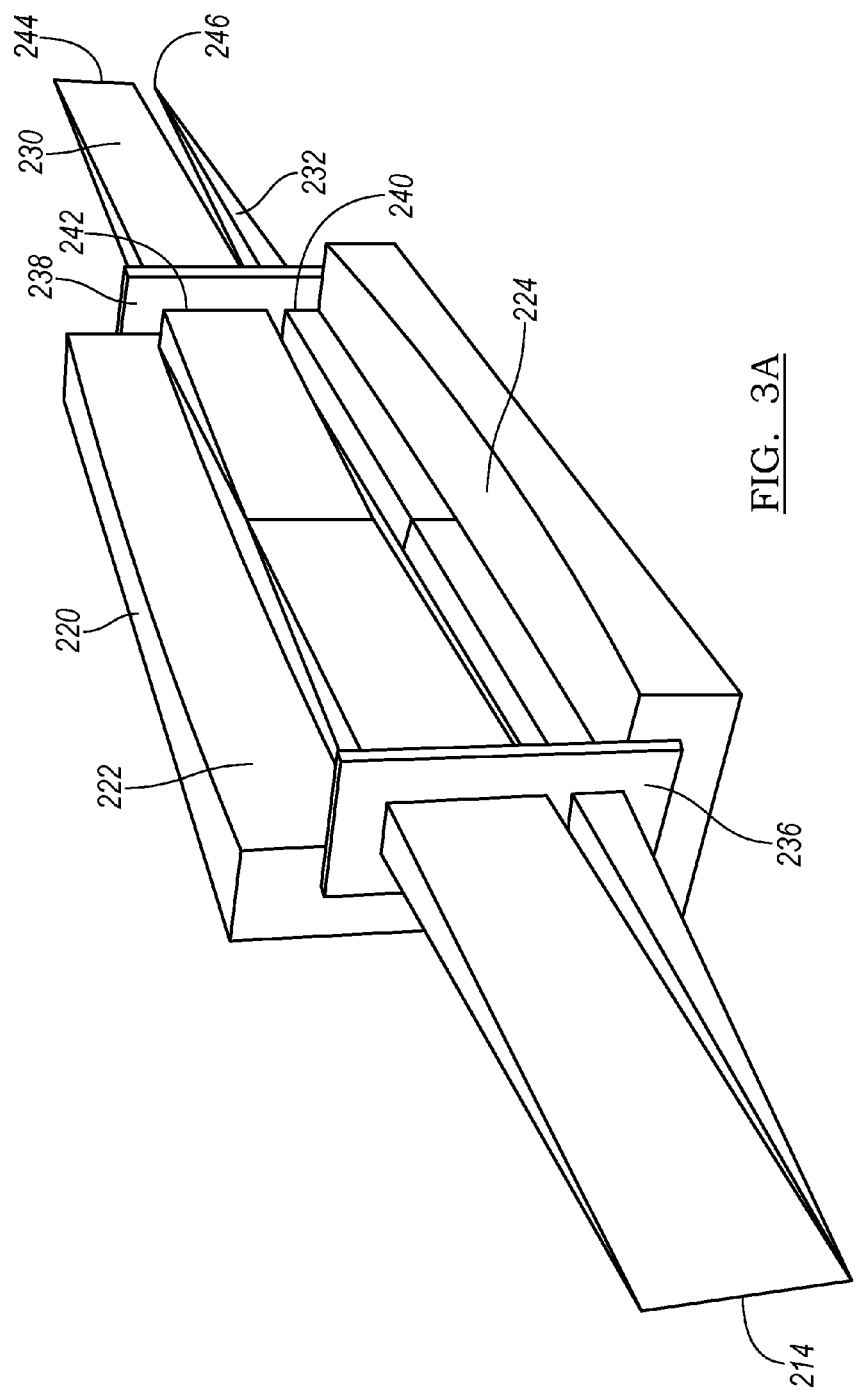
FIGS. 3A and 3B are a schematic illustration of an optical system for an x-ray scattering or diffraction using a line source.

Now referring to FIG. 3A, one possible embodiment of the x-ray source 114 and optic 116 is provided with respect to x-ray source 214 and optic 220. The source 214 is a line source which emits an x-ray beam with a line profile towards the optic 220. The x-ray beam from the source 214 interacts with an aperture 236 having a first opening and a second opening therein. The first opening may be an elongated opening allowing the x-rays that form a one-dimensional beam to pass. The second opening may be a hole, for example a square hole. Accordingly, the x-ray beam from the source 214 may be split into a first portion that forms a one-dimensional beam 230 (such as a line beam) and a second portion that forms a two-dimensional beam 232 (for example a point beam or a pencil beam or a two-dimensional beam). The first portion that forms the one-dimensional beam 230 and the second portion that forms the two-dimensional beam 232 may be received by the optic 220. The optic 220 may be comprised of two one-dimensional reflectors. One of the reflectors, for example the second surface 224, forms a two-dimensional optic with part of the other reflector, for example the first surface of the optic 222. The two-dimensional optic may be in the form of, for example, a side-by-side KB optic. In addition, part of the first reflector 222 may serve as the one-dimensional optic for the dual mode optical system. Accordingly, the source 214 and the aperture 236 may be aligned such that the one-dimensional beam 230 interacts with a first surface 222 of the KB optic while the two-dimensional beam 232 interacts with both the first surface 222 and the second surface 224 of the KB optic. Accordingly, the one-dimensional beam 230 may be conditioned, for example focused or collimated, by the first surface 222. Similarly, the two-dimensional beam 232 may be conditioned by both the first surface 222 and the second surface 224 in two perpendicular dimensions orthogonal to the direction of propagation. In some implementations, the beam selection device may be located between the optic and the sample. In the case of a line source is used, the beam selection device is preferably located between the source and the optic. In this scenario, the beams would be directed to the beam selection device, for example build into the entrance aperture 236. The exit aperture 238 may include a first opening 242 for the one-dimensional beam and a second opening 240 for the two-dimensional beam. A beam selection device in the form of a plate may be controlled to block one or both of the x-rays that form the one-dimensional beam 230 and the x-rays that form the two-dimensional beam 232, selectively. In this instance, the one-dimensional beam 230 is shown as being focused to a line 244 while the two-dimensional beam 232 is shown as being focused to a point 246. Accordingly, one of the one-dimensional beam 230 and the two-dimensional beam 232 may be selectively allowed to pass through the beam selection device and interact with sample as discussed elsewhere in this application.

In the case of a line source as shown in FIG. 3A, the optic may be aligned to the source in such a way that one of the two mirrors is in-line with the line source (or in parallel to the source), and the other mirror is aligned perpendicular to the line source. The one-dimensional beam, which is reflected by the mirror parallel to the line source only, is a typical one-dimensional beam used by many powder diffractometer. The beam can be a collimated beam or a focused beam. The divergence in the axial plane, e.g. the direction perpendicular to the diffraction plane of the mirror or in the direction of the line source, is normally defined by a slit following the optic exit. A Soller slit is also often used for further defining the axial divergence.

The two-dimensional beam may be formed with a line source by aligning the optic to any point of the line source. It may be preferred to align the optic to one end of the source to obtain a wide separation between the one-dimensional beam and the two-dimensional beam.

A beam system using a line source has much higher intensity for the one-dimensional beam than the beam system using a point source. However, the quality of the two-dimensional beam, due to the relatively lower brilliance compared to a point source and the large dimension of the source in one direction, may not be as good as when using a point source. The beam flux would be lower and the spectral background would be higher.

The fact that one mirror is aligned to be parallel to the line source and the other one is perpendicular to the line source gives the best performance for this configuration. In the diffraction plane of the mirror perpendicular to the line source, Bragg condition can be satisfied with a large portion of the source along the line source at different wavelengths, therefore a broad range of spectrum will be reflected and the beam divergence is high in this direction if we consider only one mirror. However, since the dimension of the source is small in the other direction, only the x-rays at working energy that the optic is designed for can be reflected by the mirror parallel to the line source. Consequently, the spectrum of the two-dimensional beam is largely determined by the source width of the line source, which is normally designed to be very small, for example 40 microns for a fine focus sealed tube or a long fine focus sealed tube.

An aperture with two openings, one for the one-dimensional beam and the other for the two-dimensional beam, can be used. Otherwise, the direct beam and singly reflected beam would pass though the aperture at the exit end and create noise. An aperture with two openings should also be used at the exit end of the optic to occlude the portion of the unwanted beam and block the direct beam from the source to further define the beam. A beam selection mechanism can be used before or after the optic to select either the two-dimensional beam or the one-dimensional beam for an application. It is preferred to have the beam selection mechanism installed between the source and the optic, so that when the two-dimensional beam is selected, direct beam from rest of unused source is blocked by the beam selection device.

Alternatively, a slit can be designed and applied to the optic to serve both as the beam defining aperture and the beam selection shutter. For example, a two-blade slit with a fixed long slit has the freedom to form an aperture either for the two-dimensional beam or for the one-dimensional beam before or after the optic exit. The slit can serve both functions: occlude unwanted beam, and let only one of the beams pass through. A 4-blade slit would be able to serve the same function.

Figure 3B:
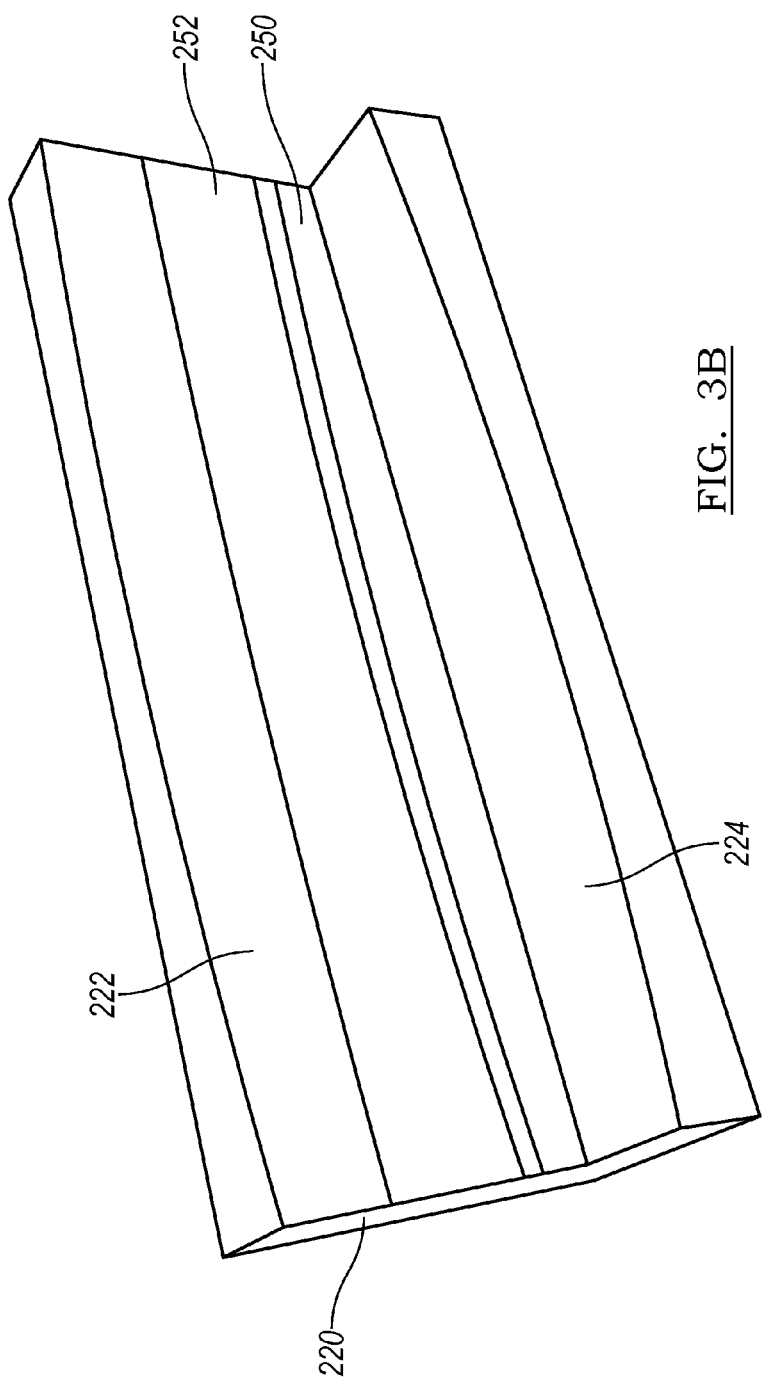

Now referring to FIG. 3B, a side view of the optic 220 is provided. A surface 222 may be perpendicular to the second surface 224. Further, both the one-dimensional beam 230 and the two-dimensional beam 232 may interact with the surface 222. The one-dimensional beam 230 may interact with a first portion of the surface 252 while the two-dimensional beam 232 may interact with a second portion of the surface 250. The first portion of the surface 252 is further away from the corner of the optic 220 than the second portion of the surface 250. In addition, the first portion of the surface 252 has no overlapping with the second portion of the surface 250. However, the first portion of the surface 252 may have a continuous contour and/or multi-layer coating as the second portion 250 of the surface 222.

Figure 4A:
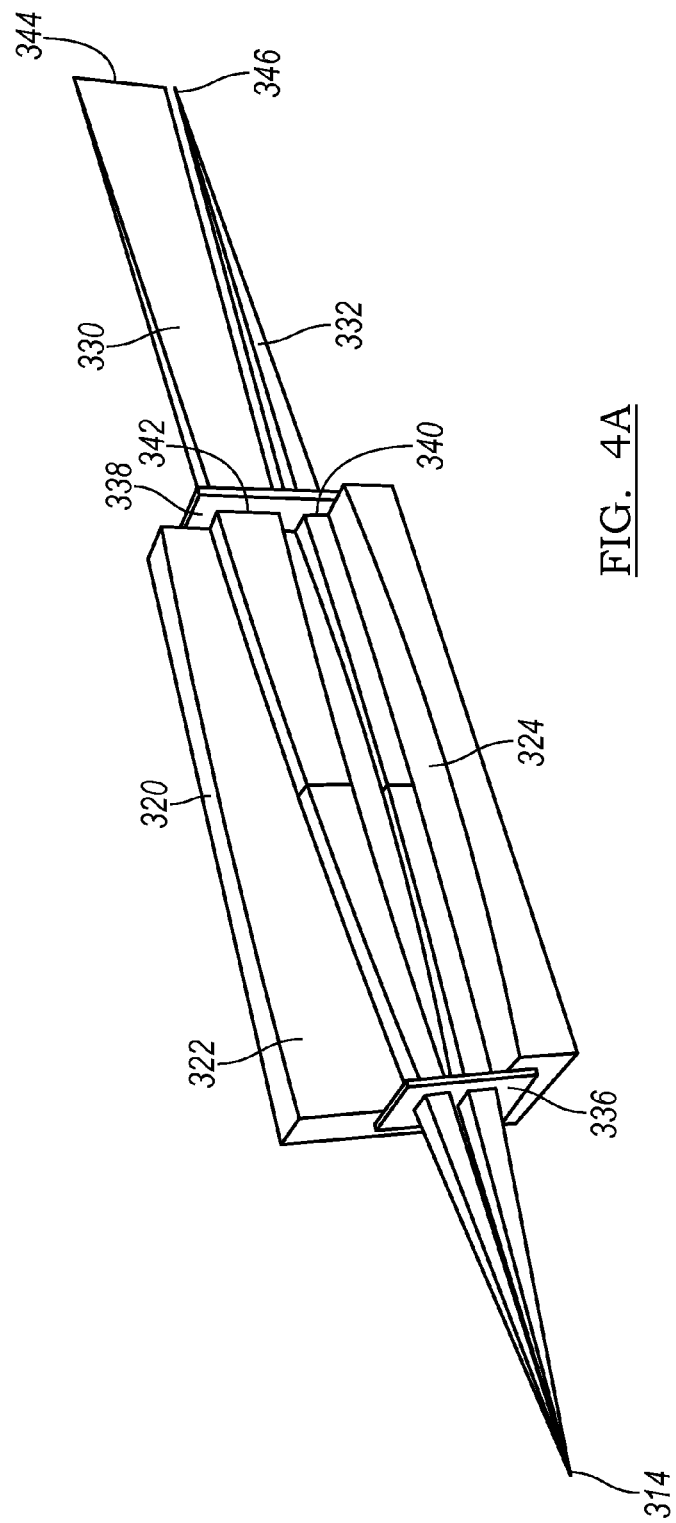

Now referring to FIG. 4A, one possible embodiment of the x-ray source 114 and optic 116 is provided with respect to x-ray source 314 and optic 320. The source 314 is a point source which emits an x-ray beam that expands from a point towards the optic 320. Accordingly, the x-ray beam from the source 314 may be split into a first portion that forms the one-dimensional beam 330 and a second portion that forms a two-dimensional beam 332. The first portion that forms the one-dimensional beam 330 and the second portion that forms the two-dimensional beam 332 may be received by the optic 320. The optic 320 may comprise two one-dimensional reflectors. The reflector 324 forms a two-dimensional optic with part of the reflector 322 in the form of, for example, a side-by-side KB optic. Part of the reflector 322 also serves as a one-dimensional optic to form a one-dimensional beam. Accordingly, the source 314 and the aperture 336 may be aligned such that the one-dimensional beam 330 interacts with a first surface 322 of the optical system while the two-dimensional beam 332 interacts with both the first surface 322 and the second surface 324 of the optical system. Accordingly, the one-dimensional beam 330 may be conditioned, for example focused or collimated, by the first surface 322 and directed to the exit aperture 338. Again, the beam selection device could also be located after the aperture and/or built into the exit aperture 338. Similarly, the two-dimensional beam 332 may be conditioned by both the first surface 322 and the second surface 324 in two perpendicular dimensions orthogonal to the direction of propagation and directed to the exit aperture. The exit aperture 338 may include a first opening 342 and a second opening 340 for the one-dimensional beam and the two-dimensional beam. The beam selection device may be controlled to block one or both of the one-dimensional beam 330 and the two-dimensional beam 332 selectively. In this instance, the one-dimensional beam 330 is shown as being focused to a line 344 while the two-dimensional beam 332 is shown as being focused to a point 346. Accordingly, one of the x-rays that form the one-dimensional beam 330 and the x-rays that form the two-dimensional beam 332 may be selectively allowed to pass through the beam selection shutter and interact with sample as previously discussed elsewhere in this application.

In the case of a point source as shown in FIG. 4A, the one-dimensional beam, which is reflected by one mirror only, is a "fan beam". Compared to the case of a line source, the two-dimensional beam with a point source may have higher intensity, and is a better defined beam spectrally and spatially. The one-dimensional beam, or the fan beam, has the merit of better spatial definition, for example, less crossed rays caused by a long source.

The point source based beam solution offers both one-dimensional beam and two-dimensional beam. The optical system is made of two reflectors. The two-dimensional function of the optical system is achieved by one reflector and part of the other reflector in a side-by-side Kirkpatrick Baez optic scheme. The one-dimensional function of the optical system is achieved by a single reflection of one of the two reflectors. The upper beam as shown schematically is a one-dimensional beam, reflected by the vertical mirror only. The beam schematically shown interacting with the corner of the optic is a two-dimensional beam, reflected by both mirrors in the orthogonal directions to form a focus. An aperture having two openings further defines the beams. The aperture shown is on both the entrance and exit side of the optic, but it could be on either the entrance side, or the exit side, or both, and is not necessarily attached to the optic. A selection mechanism, either a blade or a slit (not shown), could be used to select either the one-dimensional beam or the two-dimensional beam.

A focused beam is shown in the picture. The one-dimensional beam is divergent along the vertical direction ("fan beam") and focused in the horizontal plane. However, the two mirrors can be any combination of the elliptical mirror and parabolic mirror. The one-dimensional beam could be either a "focused fan beam" or "collimated fan beam". The two-dimensional beam could be either a focused beam, or a collimated beam, or a beam focused in one direction and collimated in the other direction.

It may be preferred to have an aperture with two openings attached on the entrance side of the optical assembly, or the exit side of the assembly, or both, and a selection device, which can be a blade or a slit, may be further incorporated into the optical system for selecting the beam. Aperture(s) attached at the entrance and exit can make the alignment much easier. A two-blade slit with a fixture slit or four-blade slit can be used to serve as the beam defining aperture as well as the beam selection device.

Now referring to FIG. 4B, a side view of the optic 320 is provided. A surface 322 may be perpendicular to the second surface 324. Further, both the one-dimensional beam 330 and the two-dimensional beam 332 may interact with the surface 322. The one-dimensional beam 330 may interact with a first portion of the surface 352 while the two-dimensional beam 332 may interact with a second portion of the surface 350. The first portion of the surface 352 may be further away from the corner of the optic 320 than the second portion of the surface 350. In addition, the first portion of the surface 352 may be non-overlapping with the second portion of the surface 350. However, the first portion of the surface 352 may have a continuous contour and/or multi-layer coating as the second portion 350 of the surface 322.

In addition, a controller may be configured to control an actuator to move the beam section device between one-dimensional operation mode and two-dimensional operation mode. Further, the controller allows automated switching between the one-dimensional operation mode and the two-dimensional operation mode based on the measurement characteristics received by the detector, for example based on scattering data such as the scattering pattern or intensity data. The controller may be also configured to communicate with a motion device, such as a motorized stage, to spin or rotate the sample either around a beam propagation axis or perpendicular to the beam propagation axis when the controller is switched to the two-dimensional mode. In addition, the controller may also control a motion device, such as a motorized stage, to move the sample between a first and second location based on the selection of the one-dimensional and two-dimensional operation mode.

Any of the controllers, control circuits, modules, servers, or engines described may be implemented in one or more computer systems or integrated controllers. One exemplary system is provided in FIG. 5. The computer system 500 includes a processor 510 for executing instructions such as those described in the methods discussed above. The instructions may be stored in a computer readable medium such as memory 512 or storage devices 514, for example a disk drive, CD, or DVD, or in some form of nonvolatile memory, internal or external to the processor, such as EPROM or flash. The computer may include a display controller 516 responsive to instructions to generate a textual or graphical display on a display device 518, for example a computer monitor. In addition, the processor 510 may communicate with a network controller 520 to communicate data or instructions to other systems, for example other general computer systems. The network controller 520 may communicate over Ethernet or other known protocols to distribute processing or provide remote access to information over a variety of network topologies, including local area networks, wide area networks, the Internet, or other commonly used network topologies.

In other embodiments, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system or processor. Further, in an exemplary, non-limited embodiment, implementations can include distributed processing, component/object distributed processing, and parallel processing. Alternatively, virtual computer system processing can be constructed to implement one or more of the methods or functionality as described herein.

Further, the methods described herein may be embodied in a computer-readable medium. The term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

As a person skilled in the art will readily appreciate, the above description is meant as an illustration the principles of this application. This description is not intended to limit the scope or application of this disclosure in that the system is susceptible to modification, variation and change, without departing from the spirit of this application.

We claim:

1. A dual mode x-ray beam system capable of providing both a one-dimensional beam and a two-dimensional beam comprising:
   an x-ray source;
   an optical system comprising two reflective x-ray optics such that
      a two-dimensional part of the optical system is formed by a first reflective x-ray optic and a first portion of the second reflective x-ray optic
      a one-dimensional part of the optical system formed by a different portion of the second reflective x-ray optic;
      a first portion of the x-rays emitted from the x-ray source is reflected by the two-dimensional part of the optical system and forms a two-dimensional beam;
      a second portion of the x-rays emitted from the x-ray source is reflected by the one-dimensional part of the optical system and forms a one-dimensional beam.

2. The beam system of claim 1, wherein the optical system of the dual mode x-ray beam system further includes a beam selection mechanism for selecting either the two-dimensional beam reflected by both reflective x-ray optics or the one-dimensional beam reflected by one reflective x-ray optic only.

3. The beam system of claim 2, wherein the beam selection mechanism is a blade which blocks either the one-dimensional beam or the two-dimensional beam.

4. The beam system of claim 2, wherein the beam selection mechanism comprises a slit and by adjusting the positions of the blades of the slit either the one-dimensional beam or the two-dimensional beam is selected.

5. The beam system of claim 2, wherein the beam selection mechanism is located between the x-ray source and the optical system.

6. The beam system of claim 1, wherein the optical system of the dual mode x-ray beam system has an aperture with two openings for further defining the output beam, a first opening of the aperture configured to receive the one-dimensional beam and a second opening being configured to receive the two-dimensional beam, the aperture being attached at an exit side of the optical system.

7. The beam system of claim 1, wherein the optical system of the dual mode x-ray beam system has an aperture with two openings for further defining the input beam, a first opening of the aperture being configured to receive the x-rays forming the one-dimensional beam and a second opening being configured to receive the x-rays forming the two-dimensional beam, wherein the aperture is attached at the entrance side of the optical system.

8. The beam system of claim 1, wherein the optical system of the dual mode x-ray beam system has two apertures, each aperture having two openings, a first opening configured for the one-dimensional beam and a second opening configured for the two-dimensional beam, one aperture being attached to the entrance side of the optical system and the other aperture being attached to the exit side of the optical system.

9. The beam system of claim 6, 7, or 8, wherein the apertures have a third opening which allows the x-rays from the source passing through directly to form a divergent beam for a Bragg-Brentano configuration.

10. The beam system of claim 1, wherein the x-ray source is a point source.

11. The beam system of claim 1, wherein the x-ray source is a line source.

12. The beam system of claim 1, wherein the dual mode x-ray beam system further includes a positioning device configured to reposition the x-ray source from a point projection to a line projection, or from the line projection to the point projection.

13. The beam system of claim 1, wherein the reflective x-ray optics form a side-by-side Kirkpatrick Baez configuration.

14. The beam system of claim 1, wherein the reflective x-ray optics of the optical system are multilayer optics.

15. The beam system of claim 1, wherein the reflective x-ray optics of the optical system are single crystal optics.

16. The beam system of claim 1, wherein the two reflective optics of the optical system is a combination of crystal optics and multilayer optics.

17. The beam system of claim 1, wherein the optical system is configured such that the one-dimensional beam is centered with the two-dimensional beam at a distance from the optic.

18. The beam system of claim 17, where the one-dimensional beam is centered with the two-dimensional beam at the sample position.

19. The beam system of claim 17, wherein the one-dimensional beam is centered with the two-dimensional beam at the detector position.

* * * * *